United States Patent [19]

Sullivan

[11] Patent Number: 5,044,953

[45] Date of Patent: Sep. 3, 1991

[54] DENTAL EVACUATOR DISINFECTANT AND FLUSH SYSTEM

[75] Inventor: Jerry Sullivan, Ridgewood, N.J.

[73] Assignee: Coltene/Whaledent, Inc., New York, N.Y.

[21] Appl. No.: 400,476

[22] Filed: Aug. 30, 1989

[51] Int. Cl.$^5$ .............................................. A61C 17/06
[52] U.S. Cl. ....................................... 433/92; 422/28; 433/91
[58] Field of Search ............... 433/91, 92; 4/261, 262, 4/263, 264; 432/1, 28, 33, 292

[56] References Cited

U.S. PATENT DOCUMENTS

| | | | |
|---|---|---|---|
| 522,842 | 7/1894 | Lawshe | 433/92 |
| 1,345,606 | 7/1920 | Leonard | 433/92 |
| 2,895,220 | 7/1959 | Johnston et al. | 433/92 |
| 3,487,573 | 11/1974 | Gandrud | 433/92 |
| 3,566,869 | 3/1971 | Crowson | 433/92 |
| 3,746,033 | 7/1973 | Keiper II | 433/92 |
| 4,054,998 | 10/1977 | Hesselgren | 433/92 |
| 4,216,185 | 8/1980 | Hopkins | 422/28 |
| 4,545,956 | 10/1985 | Ciszewski et al. | 422/28 |

FOREIGN PATENT DOCUMENTS

| | | | |
|---|---|---|---|
| 2814401 | 10/1979 | Fed. Rep. of Germany | 433/91 |
| 3514331 | 10/1985 | Fed. Rep. of Germany | 433/92 |

Primary Examiner—Cary E. Stone
Assistant Examiner—Adriene B. Lepiane
Attorney, Agent, or Firm—Helfgott & Karas

[57] ABSTRACT

A disinfectant and flush system for a dental waste evacuator comprises a container filled with disinfectant and connected to the interior of a main flow tube of the evacuator, positioned between a disposable mouth piece and a suction source. A control valve is installed between a tubing leading from the disinfectant container and the main flow tube, which ensures that the disinfectant is admitted into the main flow tube during operation of the evacuator to flush the tube continually or intermittently.

25 Claims, 3 Drawing Sheets

DENTAL EVACUATOR DISINFECTANT AND FLUSH SYSTEM

BACKGROUND OF THE INVENTION

The present invention relates to dental equipment in general, and more particularly to an evacuator disinfectant and flush system.

An evacuator is a device used by a dentist to evacuate excess saliva and debris from the mouth area while the dentist does dental work in the patient's mouth. The evacuator usually includes a disposable mouth piece in the form of an end pipe element placed in the patient's mouth and is connected to a suction source by an extended tube, and serves to suck out the waste material and saliva from the mouth area for disposal into a waste container.

While the particular pipe element inserted in the mouth is generally disposable or, at least, sterilizable, the main flow tube leading from the mouth piece to the waste container is reused as a stationary part of the evacuator and therefore builds up on its interior walls contaminants, contagious particles, etc. which can accumulate and build obstructions to the suction flow as well as providing a breeding ground for contamination and infection. A technical dental assistant is required to flush out the tubing leading to the waste container, generally once a day. However, at the end of the day there is already contamination build-up in the tubing. Furthermore, the job of flushing is a messy one which is to be avoided. In addition, the obstruction build-up may require manual cleaning of the flow tube. Also, organic tissue may accumulate in the tubing and become of such large proportions that in accordance with Federal regulations may require special handling and disposal.

Cleaning and flushing of the flow is typically carried out with special disinfectants which are stored in special containers and connected by additional tubing to the flow tube of the evacuator. Such additional tubing has also required storage and/or should be disposable.

Accordingly, there is a need to provide means that would make flushing and cleaning of the waste evacuator tubing much easier and faster and which greatly reduce the possibility of contamination and infection.

SUMMARY OF THE INVENTION

It is therefore an object of the present invention to provide a dental evacuator flushing system which provides flushing and disinfecting of the dental waste evacuator during its operation.

In brief, there is provided a flushing system which is connected to the main flow tube of the dental evacuator and includes a container filled with liquid disinfectant. A supply tube connecting the interior of the container with the main flow tube joins the main flow tube through a coupler and positioned along the main flow tube. Preferably the coupler is positioned at the junction of the flow tube and the mouth piece. A source of suction is provided to the main flow tube.

The coupler may be constructed either to allow a continual low-rate flow of disinfectant from the container into the main flow tube, or an intermittent disinfectant flow to provide periodic flushing of the system. However, in both cases, flushing of the dental evacuator is performed during its operation, whereby manual cleaning of the main flow tube would be avoided.

In an embodiment, the coupler is a T-connector having a first bore connected to the supply tube from the disinfectant container, and a second bore normal to the first bore and coinciding with the through passage between the mouth piece and the main flow tube. Normally the suction provided by the suction source of the evacuator would only be sufficient to pull in the saliva from the mouth area but insufficient to draw disinfectant into the main flow tube passage to flush the latter. However, in the arrangement according to the present invention, when some debris or excess saliva is sucked into the mouth piece, it provides an obstruction which at least partially blocks the mouth piece. This obstruction in the mouth piece cuts down the suction through the mouth piece thereby automatically increasing the suction from the disinfectant container allowing disinfectant to pass from the supply tube through the first bore of the connector into the main flow tube.

In another embodiment, the coupler has the bore connected to the disinfectant-supply tube formed as a venturi outlet which would ensure a low-rate continual flow of the disinfectant into the main flow tube.

In a further embodiment, a one-way valve, for example a spring-biased ball valve, is inserted in the bore coaxial with the through passage of the main flow tube. The ball valve only permits the disinfectant flow in a flushing direction and would prevent a reverse flow into the patient's mouth even if the patient inhales.

A disinfectant-containing jar or container may be provided separately from the main flow tube. Alternately, the disinfectant container can fit directly onto the main flow tube and includes a small pipe immersed in the disinfectant and terminating at an upper end with a bent venturi-outlet which opens into the main flow tube to pass thereinto a continuous low-rate flow of the disinfectant.

The aforementioned objects, features and advantages of the invention will, in part, be pointed out with particularity, and will, in part, become obvious from the following more detailed description of the invention, taken in conjunction with the accompanying drawings, which form an integral part thereof.

DETAILED DESCRIPTION OF THE PREFERRED EMBODIMENTS

Figure 1:
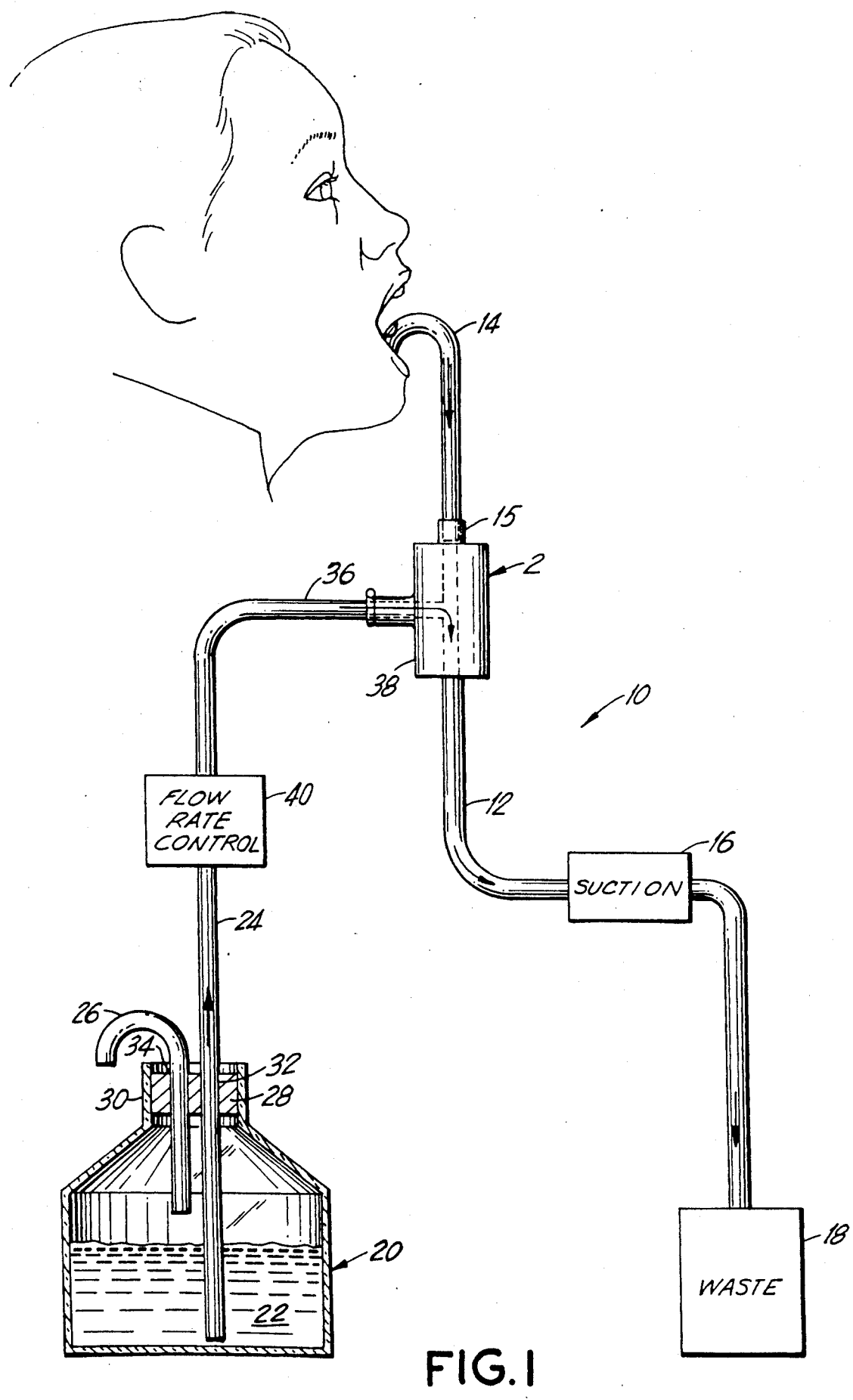
FIG. 1 is a diagrammatic view of a dental evacuator and flush system according to the present invention.

Referring now to the drawings in detail, FIG. 1 illustrates an evacuator disinfectant and flush system 10 according to the present invention. The flush system includes a main central flow tube 12. A generally disposable, or at least sterilizable mouth piece or pipe element 14 includes at its upper end a curved portion insertable into a user's mouth and its lower end 15 a connection for normal insertion into the main flow tube 12 so that mouth piece 14 is firmly held in place. A suction source 16, for example, a suction pump, is connected to the main flow tube to suck off saliva and debris from the mouth area and into a waste container designated at 18.

A separate jar or container 20 filled with liquid disinfectant 22 of any suitable conventional type is provided in the evacuator and flush system 10. A disinfectant supply tube 24 has its lower end immersed in the liquid disinfectant 22 and can draw the disinfectant or cleaning liquid into the main flow tube 12 of the system. An air vent tube 26 can be inserted with its end into the interior of container 20. The disinfectant containing jar 20 has a stopper 28 tightly closing a neck portion 30 of the jar and provided with through holes 32 and 34 for passing tubes 24 and 26 therethrough.

The end of the supply tube 24 connects into a coupler 38 installed on the main flow tube 12. A flow rate control device 40 of any suitable known type can be optionally connected in the flow path of the disinfectant.

Figure 2:
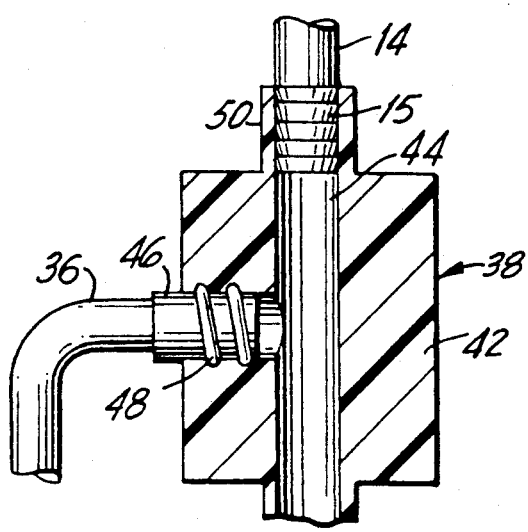
FIG. 2 is a sectional view through a detail 2 of FIG. 1, on an enlarged scale.

As best seen in FIG. 2 the coupler 38 in the embodiment illustrated is a T-connector accommodated in a housing 42 having a central vertical bore 44 formed in alignment with or as a part of the passageway of the main flow tube 12, and a substantially horizontal connector portion 46 into which the end of supply tube portion 36 connects. The supply tube can be held in place by a spring clamp 48, or other device. As shown in FIG. 2, the mouth piece 14 can have its lower end 15 removably slipped onto a threaded or serrated extension 50 provided in the bore 44 of the T-connector 38. It is, of course, understandable, that T-connector 38 can be made integral with the main flow tube 12 as an enlarged portion of the latter or separately therefrom. In the case of a separate construction sealed connections between the couple housing and the tubing are to be provided.

The operation of the evacuator disinfectant and flush system with the control T-connector is as follows: In a normal suction process, the suction provided by the source of suction 16 in the main flow tube pulls the saliva from the mouth into the disposable mouth piece 14 and then into flow tube 12 for waste disposal. However, the suction is not sufficient to draw in the disinfectant from the container 20. As debris or excess saliva from the mouth is sucked into the tube 12 it eventually provides an obstruction in the flow passage of the mouth piece pipe 14, increasing the suction to the supply tube 24 and thus to the disinfectant-containing jar 20 to thereby suck up the liquid disinfectant 22 and permit the same to pass into the main flow tube 12. This flow of disinfectant serves to flush any debris build up in the main flow tube 12 and to disinfect it thereby preventing accumulation of contaminants and avoiding infection spread. Once the obstruction is dislodged, the flow of disinfectant will stop. Thus, in the embodiment of a T-shaped connector, an intermittent flushing and disinfecting of the flow path takes place whenever an obstruction caused by debris or the like occurs during actual use of the evacuator. A flow rate control device 40 of any well known type can be optionally included. This device controls the amount of flow each time the liquid disinfectant is sucked into the tube 12.

Figure 3:
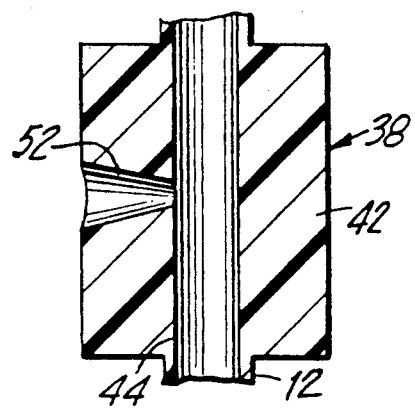
FIG. 3 is a modified embodiment of a T-connector shown in FIG. 2.

FIG. 3 illustrates an alternate embodiment of the coupler 38. The inlet portion 36 to which is connected the supply tube 24 from the disinfectant container includes a Venturi-shaped opening 52 which is in communication with the central passageway 44 formed in the valve 38, in alignment with the remaining part of the flow tube 12. A venturi effect is provided for a continuous low-rate flow of the liquid disinfectant into the main tube stream at all times, thus cleaning and disinfecting the main flow tube during actual use thereof. The flow rate will be in the droplet form but it will be continuous.

Figure 4A:
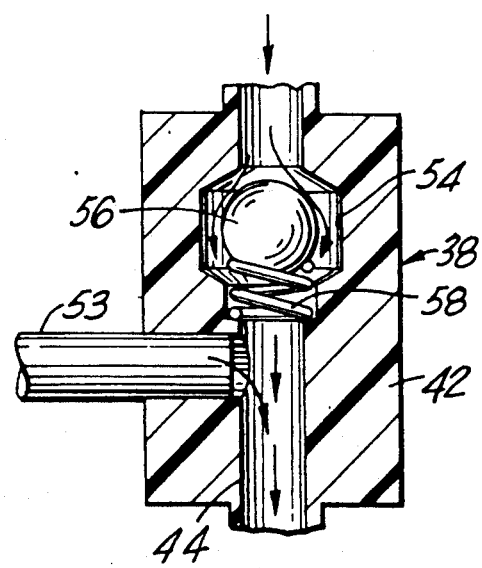
FIGS. 4a and 4b are sectional views through a one-way control valve included in the T-connector, and shown in an open and closed position, respectively.
Figure 4B:
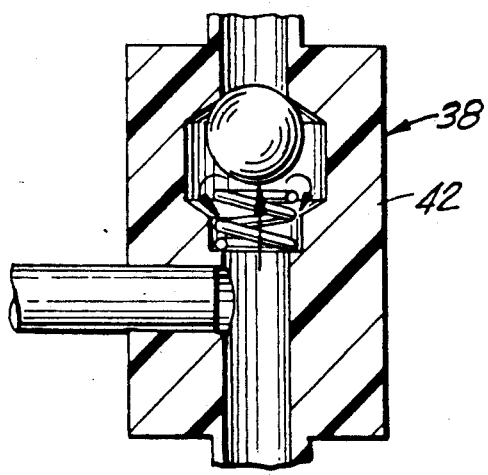

In the embodiment of the coupler illustrated in FIGS. 4a and 4b, the coupler 38 includes housing 42 which may be integral with tube 12 and is provided with two passageways 44 and 53 formed at substantially right angles to each other. Inlet tube portion 53 receives the flow of disinfectant from the supply. Central passageway 44 is formed with a cylindrical portion 54 of enlarged diameter, which receives therein a ball valve 56 biased by a spring 58 in an upward direction of closing of the valve movable within the enlarged portion 54 of the central passageway between an open position shown in FIG. 4a and a closed position of FIG. 4b. The one-way spring-loaded control ball valve permits the flow of saliva and/or debris contained therein only in the normal direction. During such normal operation, the suction downward, and the downward flow of saliva and debris operates against the biasing spring and keeps the ball valve open. Should the patient inhale, the ball valve 38 will move upwardly and close to prevent a reverse flow of the disinfectant into the patient's mouth. Normally, suction in the main flow tube 12 is sufficient to prevent any amount of disinfectant from flowing into the patient's mouth. Nevertheless one-way control valve 38 of the embodiment of FIGS. 4a and 4b can be, however, utilized to further ensure that no such disinfectant backflow occurs.

Figure 5:
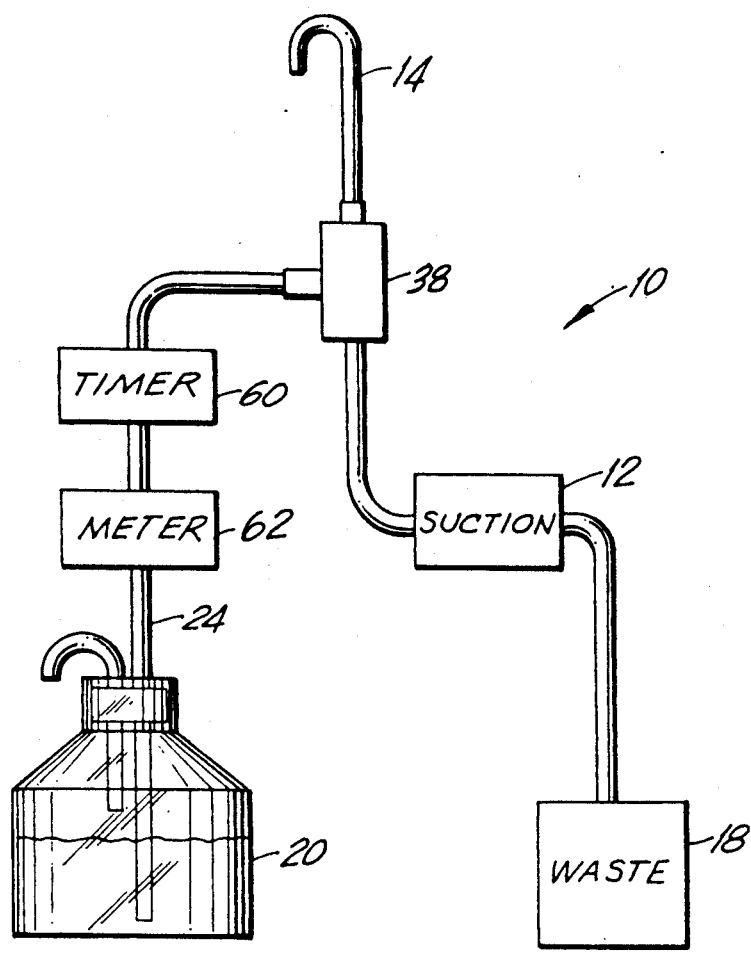
FIG. 5 is a diagrammatic view of the evacuator flushing system provided with a timer.

With reference to FIG. 5, it will be seen that a timer 60 can be added in the system between the disinfectant container 20 and the coupler 38 to provide a timed regular flushing of the system. A meter 62 may also be interconnected in the disinfectant supply tube 24 to control the amount of flushing liquid provided at periodic intervals controlled by the timer 60. The timer can be adjusted by a technician so that, for example, flushing of the system would take place every three hours, or the like.

Figure 6:
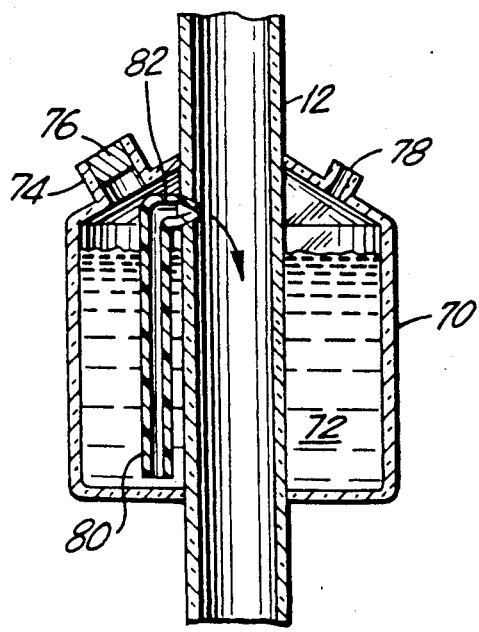
FIG. 6 is a sectional view through a container fitted directly onto a main flow tube of the evacuator and flush system, according to still another embodiment of the present invention.

FIG. 6 shows the embodiment in which, in place of a separate coupler, a container 70 filled with disinfectant 72 is fitted directly onto the main flow tube 12. A filling opening 74 is tightly closed with a stopper 76 whereas a vent air opening 78 is provided at the opposite side of the container 70. An elongated pipe 80 extending into the interior of container 70 includes an end portion 82 bent at right angles to the remaining portion thereof and opening into the interior of the main flow tube 12. End portion 82 has a venturi opening so that a continuous sucking-in of a low rate flow of disinfectant is provided throughout the entire use of the evacuator system.

In all the above described embodiments, a continual or intermittent flushing of the evacuator system during the use thereof also provides that the flow of disinfectant can break up tissue particles and prevent their accumulation into larger masses which would otherwise require special handling and disposal.

It should be understood that the diameter size of the respective passageways or tubes can be selected to determine the amount of disinfectant flow and suction amounts in the respective tubes.

While particular embodiments of the present invention have been shown as described, it will be obvious to those skilled in the art that changes and modifications may be made without departing from the invention in its broader aspects. Therefore, the aim in the appended claims is to cover all changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. An evacuator disinfectant and flush system for a dental waste evacuator having a mouth piece insertable into a patient's mouth, a main flow tube, a waste disposal connected to said main flow tube, and a suction source which sucks saliva and dental waste from a mouth area into said flow tube, the system comprising:
   disinfectant supply means;
   tube connecting means; and
   control means connectable to said mouth piece and connected to said connecting means and said main flow tube, respectively, said control means being constructed to convey saliva and dental waste from said mouth piece to said main flow tube and to control a flow of disinfectant to said main flow tube so as to permit said flow into said main flow tube during operation of the dental waste evacuator.

2. A system as in claim 1, wherein said control means is constructed so that it permits said disinfectant flow into said main flow tube when debris sucked into said mouth piece causes obstruction therein, thereby causing increase in suction in said connecting means and drawing said disinfectant from said supply means to said main flow tube through said connecting means.

3. A system as in claim 2, wherein said control means includes a T-connector having a housing formed with a first central passageway aligned with a through flow of said main flow tube and a second passageway extending at substantially right angles with said central passageway and being in communication with said tube connecting means.

4. A system as in claim 3, wherein said housing is an enlarged portion of said main flow tube.

5. A system as in claim 4, wherein said enlarged portion has a cylindrical portion for securely receiving an end of said mouth piece.

6. A system as in claim 1, wherein said control means is constructed to draw said disinfectant into said main flow tube intermittently during said operation.

7. A system as in claim 6, wherein said control means includes a one-way valve disposed in a flow passage from said mouth piece to said main flow tube.

8. A system as in claim 7, wherein said one-way valve includes a spring-biased ball valve.

9. A system as in claim 8, wherein said main flow tube includes a portion of enlarged diameter having two passageways extending at substantially right angles to each other, one of said passageways being in communication with said tube connecting means and another of said passageways being in alignment with a through flow of said main flow tube, said another passageway having an enlarged portion accommodating said one-way valve, said valve including a ball movable in dependence upon suction in said mouth piece between a closing position in which it closes said passage and an opening position in which it opens said passage to permit dental waste through said passage.

10. A system as in claim 1, wherein said control means is constructed to draw said disinfectant into said main flow tube continuously during said operation.

11. A system as in claim 10, wherein said control means includes a T-connector having a housing formed with a first central passageway in alignment with a through flow of said main flow tube and a second passageway extending at substantially right angles with said central passageway and being in communication with said tube connecting means, said second passageway being venturi-shaped to ensure a continual low rate flow into said main flow tube during said operation.

12. A system as in claim 11, wherein said housing is an enlarged portion of said main flow tube at an end thereof and receiving said mouth piece.

13. A system as in claim 1, wherein said control means is a coupler.

14. A system as in claim 13, wherein said coupler is formed integral with said main flow tube.

15. A system as in claim 1, wherein said control means is a coupler disposed between said mouth piece and said main flow tube.

16. A system as in claim 1, wherein said mouth piece is disposable.

17. A system as in claim 1, and further comprising flow rate control means incorporated in said tube connecting means between said disinfectant supply means and said control means.

18. A system as in claim 1, wherein said disinfectant supply means includes an air vent means.

19. A system as in claim 1, further comprising timer means installed in said tube connecting means to determine periodic intervals for permitting said disinfectant flow into said main flow tube so as to provide regular flushing of the system.

20. A system as in claim 19, further comprising meter means installed in said tube connecting means for controlling an amount of disinfectant admitted at said periodic intervals into said main flow tube.

21. A system as in claim 1, wherein said disinfectant supply means includes a container filled with disinfectant and disposed remotely from said evacuator.

22. A system as in claim 1, wherein said disinfectant supply means includes a container which fits onto said main flow tube and is filled with disinfectant.

23. A system as in claim 22, wherein said tube connecting means includes a tubular member immersed in said container and having at an upper end thereof a bent portion which opens into a through bore of said main flow tube.

24. A system as in claim 23, wherein said bent portion extends normal to said tubular member and is venturi-shaped, said venturi-shaped portion forming said control means to continuously draw a low-rate flow of said disinfectant into said main flow tube to flush said tube during operation.

25. An evacuator disinfectant and flush system for a dental waste evacuator having a mouth piece insertable into a patient's mouth, a main flow tube, a waste disposal, and a suction source which sucks saliva and dental waste from a mouth area into said flow tube, the system comprising:
   disinfectant supply means;
   tube connecting means in communication with said supply means and said main flow tube; and
   control means provided between said connecting means and said main flow tube for controlling a flow of disinfectant to said main flow tube to permit said flow into said main flow tube during operation of the dental waste evacuator, wherein said control means includes a T-connector having a housing formed with a first central passageway aligned with a through flow of said main flow tube and a second passageway extending at substantially right angles with said central passageway and being in communication with said tube connecting means.

* * * * *